US010758687B2

(12) United States Patent
Harris et al.

(10) Patent No.: US 10,758,687 B2
(45) Date of Patent: Sep. 1, 2020

(54) APPARATUS AND METHOD FOR PROVIDING AEROSOLIZED POWDER DELIVERY

(71) Applicant: DS-Technology GmbH, Winnenden (DE)

(72) Inventors: David Stuart Harris, Milton (GB); Philip David Canner, Knapwell (GB); Jonathan Guillaume Jamin, Bury St Edmunds (GB); Jamie Alan Greenwood, Fowlmere (GB)

(73) Assignee: DS-Technology GmbH, Winnenden (DE)

( * ) Notice: Subject to any disclaimer, the term of this patent is extended or adjusted under 35 U.S.C. 154(b) by 1009 days.

(21) Appl. No.: 15/531,831

(22) PCT Filed: Dec. 1, 2014

(86) PCT No.: PCT/GB2014/053565
§ 371 (c)(1),
(2) Date: May 31, 2017

(87) PCT Pub. No.: WO2015/082895
PCT Pub. Date: Jun. 11, 2015

(65) Prior Publication Data
US 2017/0340843 A1    Nov. 30, 2017

(30) Foreign Application Priority Data

Dec. 4, 2013  (GB) .................................. 1321398.8

(51) Int. Cl.
*A61M 15/00* (2006.01)
*A61M 11/02* (2006.01)
(52) U.S. Cl.
CPC ........ *A61M 15/0028* (2013.01); *A61M 11/02* (2013.01); *A61M 15/004* (2014.02);
(Continued)

(58) Field of Classification Search
CPC ............ A61M 15/0028; A61M 15/003; A61M 15/0031; A61M 15/0046; A61M 15/0033;
(Continued)

(56) References Cited

U.S. PATENT DOCUMENTS 6,062,213 A * 5/2000 Fuisz ................ A61M 15/0028
128/200.21
7,669,597 B2  3/2010 Sullivan et al.
(Continued)

FOREIGN PATENT DOCUMENTS

CN    101072599 A    11/2007
GB    2 404 867 A     2/2005
(Continued)

OTHER PUBLICATIONS

International Search Report of PCT/GB2014/053565, dated Feb. 18, 2015.
(Continued)

*Primary Examiner* — Bradley H Philips
*Assistant Examiner* — Vincent D Hoang
(74) *Attorney, Agent, or Firm* — Collard & Roe, P.C.

(57) ABSTRACT

An apparatus for aerosolized powder delivery includes first and second chambers containing gas at first and second pressures, respectively, above atmospheric pressure. A powder is contained within the first or second chamber. The first chamber has a first external wall and a separating wall shared with the second chamber. The first external wall or the separating wall is configured to rupture if the pressure difference across it becomes equal to or greater than a threshold pressure difference. Specifically, the apparatus is configured so that the difference between the second pressure and atmospheric pressure is greater than the threshold pressure difference. Initially, the difference between the second and first pressures is less than the pressure difference (Continued)

required to rupture the separating wall, and the difference between the first pressure and atmospheric pressure is less than the pressure difference required to rupture the first external wall.

37 Claims, 10 Drawing Sheets

(52) U.S. Cl.
CPC .... *A61M 15/0008* (2014.02); *A61M 15/0021* (2014.02); *A61M 15/0031* (2014.02); *A61M 15/0035* (2014.02); *A61M 15/0038* (2014.02); *A61M 15/0041* (2014.02); *A61M 15/0043* (2014.02); *A61M 15/0091* (2013.01); *A61M 2202/064* (2013.01); *A61M 2206/14* (2013.01); *A61M 2206/16* (2013.01)

(58) Field of Classification Search
CPC .......... A61M 15/0035; A61M 15/0036; A61M 15/0038; A61M 15/004; A61M 15/0041; A61M 15/0043; A61M 15/0048; A61M 15/005; A61M 15/0051; A61M 15/0053; A61M 15/0055; A61M 15/0056; A61M 15/0058; A61M 15/006; A61M 15/0061; A61M 15/0063; A61M 11/02; A61B 50/00; A61B 50/30; A61B 50/31; A61F 2/0095
See application file for complete search history.

(56) References Cited

U.S. PATENT DOCUMENTS

| | | | |
|---|---|---|---|
| 7,726,308 | B1 | 6/2010 | Flora |
| 2002/0092523 | A1 | 7/2002 | Connelly et al. |
| 2006/0169278 | A1* | 8/2006 | Djupesland ............ B05B 11/062 128/200.14 |
| 2006/0237010 | A1* | 10/2006 | De Boer ............ A61M 15/0028 128/203.15 |
| 2007/0099454 | A1* | 5/2007 | Gordon ............. A61M 15/0045 439/107 |
| 2007/0272763 | A1* | 11/2007 | Dunne ................ A61M 15/002 239/8 |
| 2008/0197045 | A1* | 8/2008 | Metzger ............ A61M 15/0045 206/539 |
| 2008/0283439 | A1 | 11/2008 | Sullivan et al. |
| 2011/0126830 | A1 | 6/2011 | Djupesland |
| 2011/0220234 | A1* | 9/2011 | Haas .................... A61M 15/06 138/109 |

FOREIGN PATENT DOCUMENTS

| | | |
|---|---|---|
| GB | 2 444 395 A | 6/2008 |
| WO | 2005/021059 A1 | 3/2005 |

OTHER PUBLICATIONS

Written Opinion of the International Searching Authority of PCT/GB2014/053565, dated Jun. 11, 2015.
Chinese Office Action dated Oct. 11, 2019 in Chinese Application No. 201480084543.4 with English translation.

* cited by examiner

APPARATUS AND METHOD FOR PROVIDING AEROSOLIZED POWDER DELIVERY

CROSS REFERENCE TO RELATED APPLICATIONS

This application is the National Stage of PCT/GB2014/053565 filed on Dec. 1, 2014, the disclosure of which is incorporated by reference. The international application under PCT article 21(2) was published in English.

The present invention relates to an apparatus for use in aerosolized delivery of a powder, a method for providing aerosolized powder delivery and a device to provide aerosolized powder delivery. Embodiments described relate, in particular, to an apparatus for providing aerosolized delivery of a medicament in dry powder form.

BACKGROUND OF THE INVENTION

Inhalers are commonly used to deliver drugs into the body via the lungs, typically for treating conditions such as asthma and Chronic Obstructive Pulmonary Disease (COPD).

The most common type of inhaler is the so-called metered dose inhaler (MDI) in which the drug to be delivered is stored in solution or suspension in a pressurized container that contains a propellant. In use, the MDI releases the drug in an aerosol. Another type of inhaler is the dry powdered inhaler (DPI) in which a drug in powder form is delivered to a patient. Generally, dry powder drug formulations have the advantage over solutions or suspensions in that they are usually more stable during storage and therefore offer a longer shelf life.

The use of inhalers to deliver drugs in this way has several advantages over other drug delivery methods, such as injections. In particular, inhalers enable rapid onset of relief, the drugs being delivered are not metabolised before entering the blood of a patient, and delivering drugs in this way is not painful or, indeed, even uncomfortable.

In contrast, injections where drug formulations are delivered in liquid form (either as a solution or a suspension) can be painful when administered and often require cold storage, which is particularly the case for vaccines. This is a particularly costly disadvantage when shipping vaccinations around the world, as they must be kept sufficiently cold throughout the entire journey. Sharing needles used for injections can spread infectious diseases, which is a particularly recognised problem in developing countries. So called needlestick injuries, where a health care worker administering the injection is injured by the needle from the injection are also seen as a threat posed by injections.

Because of the numerous advantages of using inhalers, and DPIs in particular, to deliver drugs fast and effectively, there is much research into developing dry powder formulations to treat therapies beyond asthma and COPD. For example, the systemic delivery of drug molecules via the pulmonary route could be used to alleviate chronic pain (such as, breakthrough cancer pain), or DPIs could be used for needleless administration of insulin for the treatment of diabetes.

Many of these drug formulations undergoing development need to be delivered in quantities much higher than the typical doses of several tens or hundreds of micrograms required for treating asthma and COPD. For this reason, there is a drive to create respirable "engineered" drug formulations, which do not use the carrier particles (usually lactose) that are typically usually used for DPIs used for treating asthma and COPD.

The majority of DPI devices currently on the market are 'passive' devices, which are solely reliant on the inspiratory energy of the patient to create a respirable aerosol. Passive DPIs to date have typically been developed to deliver blended dry powder formulations, which use relatively large (50 to 300 µm) lactose carrier particles to bulk up the volume of each dose (typically micrograms) of active pharmaceutical ingredient (API). This improves metering accuracy for small doses (as well as aiding powder handling during manufacture, for example, by improving the flowability of the blend). Even for higher doses, a carrier can still be beneficial, as it is extremely difficult to aerosolise pure API using only the inspiratory power from the patient.

In order for the small API particles to reach the deep lung, the aerosolization engine of the DPI must somehow detach the pure drug from the carrier particle on inhalation. Most aerosolization engines within passive DPIs use combinations of impact and shear forces to break-up, disperse and aerosolise formulations. Even the most effective passive DPIs, however, cannot ensure complete deagglomeration of drug and carrier particles on delivery, and the majority of pure drug delivered from the device (typically 70-80%) remains attached to the larger carrier particles. Rather than being delivered to the deep lung for treatment, these combined particles impact on the mouth and throat, both wasting the drug and potentially leading to unwanted side effects.

To avoid this problem with deagglomeration, it would be desirable to deliver API-only formulations of drug from a DPI. The problem with this is that while aerosolization engines including swirl chambers, cyclones and similar are effective for carrier-based formulations, they do not work well with API-only formulations, as the presence of the large carrier particles has a significant impact on the operation of the DPI. For example, without the presence of larger carrier particles API would accumulate at the walls, where it is not exposed to the aerodynamic drag caused by the airflow (as the size of respirable particles is smaller than the thickness of the boundary layer), and can be held there by a combination of Van der Waal's, electrostatic and surface energy forces. These close-acting forces can vary depending upon, for example, environmental conditions and consequently the accumulated fraction of deposition can be thought of as 'fragile'. For example, the impact created by knocking or dropping the inhaler could dislodge the deposition (unknown to the user), who could then receive a much higher dose than expected. This would mean that the inhaler product would (rightly) fail the mandatory dose content uniformity requirements, and not be approved for regulated markets. This is a significant reason why current DPIs that use relatively large carrier particles for the API are not necessarily suitable for delivering API-only formulations.

The use of carrier particles greatly increases the costs of formulation development of drugs for use in DPIs, due to the need to create a homogeneous blend of API with the carrier excipient. Particles also have to be made smaller than necessary to account for incomplete deagglomeration by the device engine, and the stability of the carrier-API mix must be ensured. Furthermore, poor carrier-API deagglomeration means that the best passive DPIs (using a carrier) currently available are typically no more than 50% effective or, in other words, 50% of the drug (API) is wasted in normal use.

Although passive devices are low cost, their performance is typically limited by the underlying physics, and they typically require high formulation development costs. A further disadvantage of passive devices is that the delivered dose of API is highly dependent on the inhalation strength of the user, which may not be sufficient in patients who are unwell, elderly or very young.

For these reasons, the delivery of active pharmaceutical (API)-only engineered formulations, for DPI therapies beyond asthma and COPD, requires different device technology to carrier-based DPIs.

In order to meet this demand, 'active' dry powder inhalers capable of delivering API-only formulations are under development as an alternative to passive DPIs. Rather than relying on the inspiratory effort of the user, active DPIs provide the power to aerosolise and deliver the API by another means, leading to a uniform and repeatable drug-delivery step that is independent of the inhalation strength of a user. This power may be provided, for example, via electricity from a battery or from compressed air. Active delivery provides huge performance advantages, but existing devices are complicated to use and manufacture, and as a result are costly for both companies and patients. Due to the high complexity and expense of active DPIs, there are currently no active devices on the market.

Development is currently divided between passive devices with limited performance but a low cost, and active devices that offer high performance, but at a much higher cost. There is therefore a great demand for a device that combines the high performance of active delivery with the low cost and simplicity of passive delivery.

BRIEF SUMMARY OF THE INVENTION

The invention in its various aspects is defined in the independent claims below, to which reference should now be made. Advantageous features are set forth in the dependent claims.

In a first aspect, the invention provides an apparatus for use in aerosolized delivery of a powder, comprising a first chamber, containing gas at a first pressure higher than atmospheric pressure, and a second chamber, containing gas at a second pressure higher than atmospheric pressure. The apparatus also comprises a powder, contained within the first or second chamber. The first chamber has a first external wall and a separating wall, the separating wall being shared with the second chamber. The first external wall or the separating wall is configured to rupture if the pressure difference across it becomes equal to or greater than a threshold pressure difference. In particular, the apparatus is configured so that the difference between the second pressure and atmospheric pressure is greater than the threshold pressure difference. In an initial state, the apparatus is configured such that the difference between the second pressure and the first pressure is less than the pressure difference required to rupture the separating wall, and the difference between the first pressure and atmospheric pressure is less than the pressure difference required to rupture the first external wall.

Both first and second chambers are pre-pressurised to pre-determined pressures above atmospheric pressure, so that the pressure difference across the separating wall may be positive, negative or zero, depending only on the relative magnitudes of the first and second pressures.

As long as the pressure difference across a particular wall of the apparatus is less than a threshold pressure difference at which the wall would rupture the apparatus will remain stable. If the pressure on one side of a wall changes so that the pressure difference across the wall will exceeds the threshold pressure difference of that wall, the wall ruptures. Once the wall ruptures, the gas at the higher pressure expands through the space left by the ruptured separating wall.

In a first preferred embodiment of an apparatus in accordance with the present invention, the first external wall is configured to be ruptured. The first external wall has a point or points of relative weakness at the intended rupture position. One way in which the first external wall can be ruptured is by pressing on the first external wall on or near to the point or points of weakness. This creates tension in the wall such that a split forms at the point or points of weakness. Alternatively a piercing or peeling operation could be performed. When the first external wall is ruptured, the pressure in the first chamber drops rapidly. The pressure difference across the separating wall then becomes far greater than the threshold pressure difference of the separating wall, and the separating wall ruptures. The separating wall and/or the first external wall may be provided with a point or points of relative weakness, for example using score lines, laser etched lines or kiss-cuts, in order to ensure the separating wall bursts in the desired manner. The inventors have found that with this construction of apparatus, rather than simply splitting or breaking slightly, the separating wall bursts catastrophically, so the separating wall is displaced to a position in which that they no longer obscure the opening between chambers. With the use of score lines or kiss-cuts, any split in the separating wall propagates along the score lines. The separating wall may remain attached to the rest of apparatus at its periphery but is pushed or folded out of the way of the escaping gas. In the event of a catastrophic failure, or burst, of the separating wall, the gaseous contents of the second chamber expand rapidly through the opening, effectively aerosolizing the powder and carrying it out of the apparatus. As an alternative, or in addition, to creating points of weakness using cutting scoring or etching, portions of the first external wall or separating wall may be strengthened, for example by adding additional layers or materials. This has the same effect of ensuring that particular portions of the wall are weaker than others and so will rupture first under pressure.

In certain preferred embodiments the apparatus may take the form of a conventional blister pack, with the cold-formed blister cavity comprising a second external wall. The first external wall may be made of lidding foil, or another laminated foil, as used in a typical blister pack. It may also be hermitically sealed around the edges of the blister pack with a heat seal or other such air-tight seal. The first external wall may be kiss-cut, scored or laser-etched at a specific position. This introduces an intended point of weakness at an intended rupture position, helping to ensure that the wall ruptures in the desired fashion. This step is advantageously carried prior to assembly of the apparatus. The edges of the apparatus may comprise a flange.

The separating wall inside the apparatus may be formed from a lidding foil, or another laminated foil, used in conventional blister manufacture. It may also be sealed around its periphery to the walls of the blister pack (the second external wall), so that both first and second chambers are hermitically sealed. The separating wall may also be kiss-cut, scored or laser-etched at a specific position. This step is advantageously carried prior to assembly of the apparatus. This scoring or laser-etching introduces an intended point of weakness, so can be used to weaken the wall at the intended rupture point. This helps to ensure that the wall ruptures in the desired fashion.

The use of laminated foils, in particular including one or more polymer layers, for the walls that rupture reduces the possibility that fragments of those walls will break away from the apparatus and be delivered with the powder.

The separating wall and the first external wall may have the same threshold pressure difference. Alternatively, one may have a lower threshold pressure difference than the other.

The powder may be formed into a pellet or puck before being placed in the apparatus to improve handling. In certain preferred embodiments, the powder is held in the second chamber.

In a particularly preferred embodiment, the powder may be held apart from the second external wall forming the outside of the apparatus. Holding the powder centrally, away from any non-rupturing walls allows expanding gas to flow both through and around the powder, leading to improved aerosolization.

The powder may be held on a gas-permeable structure, such as filter media such as porous paper, or a mesh material made from polyester, nylon or paper, so that gas exiting the second chamber may travel through and around the powder, entraining and aerosolising the powder in a stream of expanding gas. This gas-permeable structure may be held close toot the separating wall or the first external wall. The gas-permeable material may be shaped so as to form a container, in which the powder may be situated. The gas-permeable structure may be coupled to the separating wall or first external wall in such a way that the separating wall effectively seals the powder inside this container.

The powder contained in the apparatus may be a powdered therapeutic agent, such as a medicament. As used herein, the term "therapeutic agent" includes any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. It also includes compounds administered to an organism as a placebo. The therapeutic agent may consist of an active pharmaceutical ingredient without carrier particles.

The interior of the apparatus may comprise an inert gas or gases, such as nitrogen, carbon dioxide or air. In particular, the chamber containing the powder may be filled with a gas or gases that do not react with the active pharmaceutical compound during storage.

The apparatus may additionally comprise a third chamber at a third pressure higher than atmospheric pressure. In this embodiment, the apparatus is configured such that the first and second chambers share a first separating wall, while the second and third chambers share a second separating wall. The second separating wall is preferably parallel to the first separating wall. The second separating wall may have a point of weakness at an intended rupture position. The second separating wall may be kiss-cut, scored or laser etched at the intended rupture position. The third pressure may be higher than the first and second pressures. The powder may be held in the third chamber.

This second embodiment may be configured such that rupture of the first external wall causes a drop in the first pressure of the first chamber, so that the pressure difference across the first separating wall exceeds its threshold pressure difference. This causes the catastrophic rupture of the first separating wall, in turn leading to the pressure difference across the second separating wall exceeding its respective threshold pressure difference. This leads to the catastrophic rupture of the second separating wall resulting in the expulsion of the contents of the third chamber. Additional separating walls may be added in the same manner to provide any number of cascaded chambers.

An apparatus of the first or second embodiment may additionally comprise an internal piercing element contained within one of the chambers. For example, in a two chamber embodiment, the internal piercing element may be disposed on a wall of the second chamber so that a sharpened end of the piercing element points towards the separating wall. An application of pressure to the wall of the second chamber of the apparatus then causes the internal piercer to contact and break the separating wall. Gas at the higher second pressure then expands rapidly into the first chamber, equalising the pressures in the two chambers. The apparatus is configured so that the newly equalised pressure exceeds the threshold pressure of the first external wall, which therefore ruptures catastrophically.

The second external wall of the apparatus may be formed from a deep-drawn can. This allows the apparatus to have a greater volume in relation to its diameter when compared to a cold-formed or thermo-formed second external wall. This allows the apparatus to store more energy, which may provide benefits to the aerosolization and powder delivery processes, particularly if a large mass of powder is to be delivered.

A release of pressure in the chamber holding the powder, by rupturing an external or separating wall, aerosolizes the powder and forces it from the apparatus. The release of gas pressure between the powder particles is particularly beneficial in this process as it pushes the particles apart.

An apparatus in accordance with the invention addresses the problem of delivering relatively large payloads of carrier-free drug formulation in an efficient and low-cost manner. An inhaler using an apparatus in accordance with the invention can deliver respirable powdered drug formulation very efficiently. The inventors have found that with this construction of apparatus, rather than simply splitting or breaking slightly, the second and subsequent walls to rupture fail catastrophically, so that pressure is released suddenly and the wall is displaced so that there is little or nothing of it in a position that obscures the opening between chambers. It is preferable that the walls remain attached to the apparatus and are not delivered with the powder.

One advantage of an apparatus in accordance with the invention is that it is particularly effective at dispersing and aerosolizing very fine powdered medicament, whilst minimising deposition within an inhaler airway or output and also the mouth (buccal cavity) of the user. This increases, and potentially maximises, the overall efficiency of the inhaler product. The arrangements described herein are particularly suited to the aerosolization of formulations that contain only a respirable size fraction. They are highly efficient. They provide an efficacious and consistently delivered fine particle dose. They provide very low inhaler or oropharyngeal deposition leading to low wastage.

In a second aspect of the present invention, there is provided a method for providing aerosolized powder delivery, comprising the step of acting on an apparatus in accordance with the first aspect of the invention to break one of the first external wall or separating wall, so that a pressure difference across the other of the first external wall or the separating wall exceeds the threshold pressure difference. The step of acting on the apparatus may comprise moving the apparatus into contact with a pressing, piercing, cutting or peeling element, by moving the apparatus, the pressing, piercing, cutting or peeling element, or both. Alternatively, the step of acting on the apparatus may comprise compressing the apparatus, particularly if the apparatus comprises an internal piercing element.

In a third aspect of the present invention, there is provided a device to provide aerosolized powder delivery, comprising: an apparatus in accordance with the first aspect of the invention and a housing, the housing comprising a hollow body with a mouthpiece disposed at a first end of the hollow body element. The device further comprises a means to break one of the first external wall or the separating wall of the apparatus, so that a pressure difference across the other of the first external wall or the separating wall exceeds the threshold pressure difference and the powder is aerosolized and delivered towards the mouthpiece.

The device may be a dry powder inhaler. The means to break one of the first external wall or the separating wall may be actuated by a user sucking on the mouthpiece.

The means to break may be a pressing or piercing element. In one embodiment of the device, the means to break one of the first external wall or the separating wall comprises a blunt pressing element within the hollow body and configured to rupture the first external wall of the apparatus when first external wall is brought into contact with the pressing element with a sufficient force.

The device may additionally comprise: a sliding carriage element held within the housing, the apparatus being held on the sliding carriage element, wherein the pressing element is positioned within the housing, and wherein the sliding carriage can move within the housing from an initial position in which the apparatus is held apart from the pressing element to a delivery position in which the apparatus contacts the pressing element.

The device may be configured such that suction on the mouthpiece moves the sliding carriage from the initial position to the delivery position. The pressing element is advantageously positioned between the sliding carriage and the mouthpiece. The housing may include a carriage stop surface to prevent the carriage moving beyond a stop position towards the mouthpiece, wherein the pressing element does not pierce the chamber containing the powder as the sliding carriage moves to the stop position. The sliding carriage may be free to recoil when the apparatus is ruptured. This will reduce the speed of delivery of the powder relative to the mouthpiece, which may be desirable.

The device may advantageously further comprise a vortex generator element within the housing, such that an aerosolized drug formulation exiting the apparatus is funnelled by the vortex generator element in order to form a vortex of aerosolized drug. The vortex generator may be provided on the sliding carriage.

Alternatively, the means to break may be a compression element. This is advantageous for use with apparatus having an internal piercing element. In a second embodiment of the device, the means to break one of the first external wall and the separating wall comprises a compression element which, optionally in combination with an internal piercing element of the apparatus, provides a means to break the separating wall of the apparatus. The means to break may be a spring loaded compression element that is released by a user sucking on the mouthpiece.

Features described in relation to one aspect of the invention may be applied to other aspects of the invention.

BRIEF DESCRIPTION OF THE DRAWINGS

The invention will be described in more detail, by way of example, with reference to the accompanying drawings, in which.

DETAILED DESCRIPTION OF THE INVENTION

Figure 1:
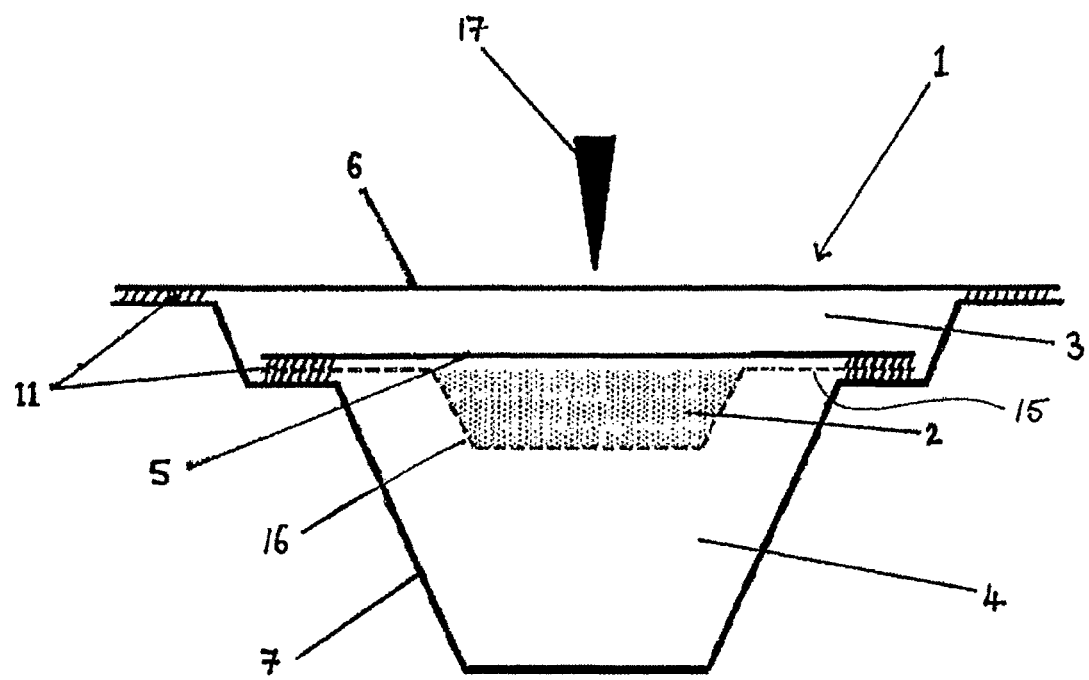
FIG. 1 shows a cross section through a first embodiment of an apparatus in accordance with the present invention.

Apparatus for use in aerosolized delivery of a powder in accordance with the present invention will now be described with reference to FIGS. 1 to 11. The apparatus are suitable for use in medical devices, particularly aerosol drug delivery devices, particularly inhalers particularly dry powder inhalers.

In the first embodiment described in FIGS. 1 to 5, the apparatus 1 for aerosolized delivery of a pharmaceutically active compound 2 comprises a first chamber 3 and a second chamber 4, wherein the first chamber 3 contains gas at a first pressure higher than atmospheric pressure, and the second chamber 4 contains gas at a second pressure higher than atmospheric pressure. The apparatus 1 also comprises a powder contained within the first or second chamber. The first and second chambers are both contained within the apparatus and are separated by a separating wall 5. This connecting or shared wall 5 is configured to rupture if the pressure difference across it becomes equal to or greater than a threshold pressure difference. This threshold pressure difference may conveniently be referred to as the 'rupture pressure' of the separating wall.

The first pressure of the first chamber 3 may be higher than the second pressure of the second chamber 4. Alternatively, the first pressure of the first chamber 3 may be lower than the second pressure of the second chamber 4. Alternatively, the first pressure of the first chamber 3 may be equal to the second pressure of the second chamber 4.

If the pressure in the first chamber 3 drops rapidly, and to a sufficient extent that the pressure difference across the separating wall becomes greater than the threshold pressure difference, the separating wall 5 may rupture catastrophically. If the first pressure suddenly drops to atmospheric pressure, then the pressure difference across the separating wall 5 does exceed the threshold pressure so that rather than simply tearing or breaking slightly, the separating wall bursts catastrophically, so that the split portions of the separating wall are folded back and do not significantly obscure the opening between chambers. In the event of a catastrophic failure, or burst, of the separating wall, the gaseous contents of the second chamber 4 expand rapidly through the opening, pushing any remnants of the separating wall 5 and the first external wall 6 out of their path.

In the first embodiment, the first chamber comprises a first external wall 6 configured to be ruptured. FIG. 1 is a cross section of the first embodiment of the apparatus 1, shown before the powder is aerosolized and delivered out of the apparatus. The apparatus 1 comprises a first external wall 6 and a second external wall 7, which are hermetically sealed around its periphery by heat seals 11. The interior of the apparatus comprises a first chamber 3 containing air at a first pressure higher than atmospheric pressure, and a second chamber 4 containing air at a second pressure higher than atmospheric pressure. The first chamber is separated from the second chamber by a separating wall 5, hermetically sealed around its periphery to the second external wall 7 of the apparatus. The separating wall 5 can withstand pressure differences up to a threshold pressure difference. In FIG. 1, the difference in the first and second pressures of the gases is less than the threshold pressure difference. But the second chamber is pressurised such that the difference between the second pressure and atmospheric pressure is greater than the threshold pressure difference of the separating wall.

In this embodiment, the apparatus comprises a blister pack, wherein the second external wall is comprised of a cold-formed foil blister back. The cold-formed foil comprises at least one layer of aluminium and one or more external layers of polymer. The edges of the apparatus comprise a flange. The first external wall 6 and separating wall 5 are formed from laminated, lidding foil that comprises a layer of aluminium and one or more thermoplastic layers capable of forming a heat seal. The first external wall, second external wall and the separating wall all provide a gas barrier.

The blister back is shaped to provide shelves to which the separating wall and first external wall are sealed. The separating wall and first external wall are arranged to extend parallel to one another. In this embodiment, the first external wall and separating wall are sealed to separate shelves in the second external wall. However, it is possible for the separating wall to be sealed to the second external wall and the first external wall to be sealed to the separating wall at its periphery. The separating wall or first external wall may be shaped to provide a desired volume for the first chamber.

The first external wall may be scored or laser-etched at a specific position 12. This scoring or laser-etching introduces an intended point of weakness, so can be used to weaken the first external wall at the intended rupture point 13. Similarly, the separating wall may also be scored or laser-etched at a specific position 14. This scoring or laser-etching introduces an intended point of weakness, so can be used to weaken the separating wall at the intended rupture point 13.

In the first embodiment, the powder 2 is held in the second chamber 4. The powder is held on a gas-permeable material 15, in this embodiment a nylon mesh, so that gas exiting the second chamber may travel through and around the powder 2, entraining and aerosolising the powder in a directed stream of expanding gas 10. The gas permeable membrane may alternatively be formed from a permeable membrane, or from gas permeable paper, or from a mesh of another material, such as polyester.

This gas-permeable material 15 is coupled to the separating wall 5. In this embodiment, the gas-permeable material is sealed between the separating wall and the second external wall when they are heat sealed to one another. The powder 2 is advantageously held apart from the second external wall forming the outside of the apparatus. The powder may be formed into a pellet to improve handling. The gas-permeable material is shaped so as to form a container 16 in the centre of the apparatus, in which the powder 2 is held. The gas-permeable material 15 may be held close to the separating wall in such a way that the separating wall effectively seals the powder inside the container 16. Holding the powder centrally allows expanding gas to flow both through and around the powder, leading to improved aerosolization.

The powder 2 may comprise a powdered therapeutic agent, such as a medicament, which may contain one or several pharmaceutically active ingredients. The powder may also comprise other pharmaceutically inactive ingredients, including carrier particles such as lactose.

The pressure in the second chamber is preferably at least 50 kPa above atmospheric pressure, and more preferably at least 300 kPa above atmospheric pressure. In this embodiment, the pressure in the second chamber is about 500 kPa and the pressure in the first chamber is about 250 kPa. The pressure difference between the second pressure and atmospheric pressure is preferably at least 20% greater than the threshold pressure difference of the separating wall 5, and more preferably 50% greater than the threshold pressure difference. In this embodiment the threshold pressure difference is 300 kPa. In general, the separating wall is configured such that its threshold pressure difference is preferably between 50 kPa and 1000 kPa, and most preferably between 100 kPa and 500 kPa.

FIG. 1 also shows a pressing element 17, which does not form part of the apparatus 1.

Figure 2:
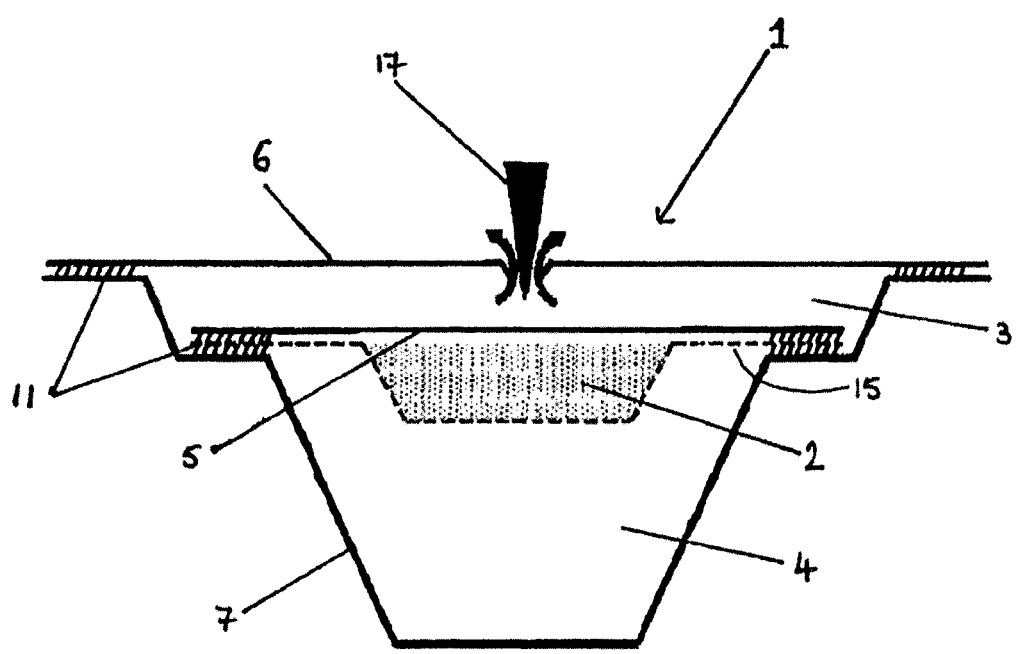
FIG. 2 shows a cross section through the apparatus of FIG. 1 as said apparatus is ruptured by an external element.

FIG. 2 shows a cross section of the first embodiment of the apparatus 1 as it is pierced by the pressing element 17. In alternative embodiments, the first external wall may alternatively be ruptured by other means such as piercing, tearing or peeling.

Rupturing the first external wall by pressing, piercing, tearing or puncturing, as shown in FIG. 2, will allow gas to escape, leading to the catastrophic failure of the separating wall 5. The parallel configuration of the connecting and first external wall means that the rapidly expanding gaseous contents of the second chamber exit the second chamber through the ruptured separating wall 8, and continue out of the first chamber through the ruptured first external wall 9. The contents of the second chamber thus exit the apparatus in a directed cloud of expanding gas 10, forcing aside any remnants of the ruptured first external wall.

The pressing element impacts the device close to the intended rupture point 13 creating tension in the first external wall. In order to ensure a clean rupture the first external wall 8 is kiss-cut to weaken it at the intended rupture position, as previously described. The intended rupture position is preferably in the centre of the first external wall.

The tension produced by the pressing element causes the first external wall to split at the point of weakness and the split rapidly propagates along the lines of weakness produced by the kiss-cut.

The separating wall 5 is also kiss-cut to weaken it at an intended rupture position so that it splits in the same manner. The intended rupture position is in the centre of the separating wall.

In this embodiment the pressing element is blunted, so that it connects with the first external wall and applies a pushing force close to the intended rupture point. This creates tension in the wall so that it splits at the intended rupture point. The split then propagates along the pre-scored sections. Alternatively, a sharp piercer may be used, which tears the first external wall at its point of contact.

FIG. 2 shows that at the point of initial rupture, the gaseous contents of the first chamber escape rapidly through the opening in the ruptured wall. As a result, the pressure of the first chamber 3 decreases rapidly from the first pressure to atmospheric pressure. As the gas escapes from chamber 1, the pressure difference across the separating wall 5 increases. At the instant shown in FIG. 2, the pressure difference across the separating wall has not yet reached the threshold pressure difference at which the separating wall will rupture.

As the pressure in the first chamber rapidly drops to atmospheric pressure, the pressure difference across the separating wall 5 rapidly becomes greater than the threshold pressure difference. This pressure difference is greater than the separating wall can withstand, and the wall bursts catastrophically. Due to the kiss-cut weakness at the rupture position, the wall ruptures outwards from its centre.

Figure 3:
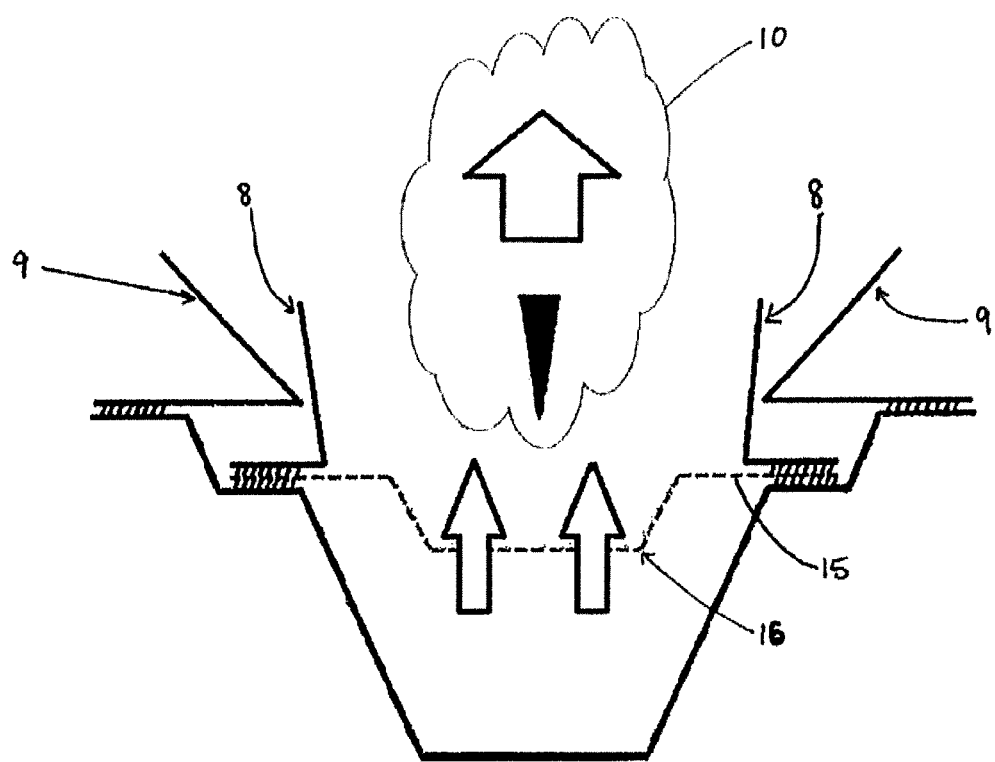
FIG. 3 shows a cross section through the apparatus of FIG. 1 immediately following rupture by the external element as shown in FIG. 2.

FIG. 3 shows the same apparatus an instant later, immediately following the catastrophic rupture of the separating wall 5. As the separating wall bursts, the pressurised gas in the second chamber expands out of the newly-created opening. The sudden release of pressure in the second chamber aerosolizes the powder and forces it from the apparatus. The release of gas pressure between powder particles pushes the particles apart. The rapidly expanding gas forces the remnants of the ruptured connecting and first external walls out of the way, and a cloud of aerosolized powder is ejected from the apparatus.

Figure 4:
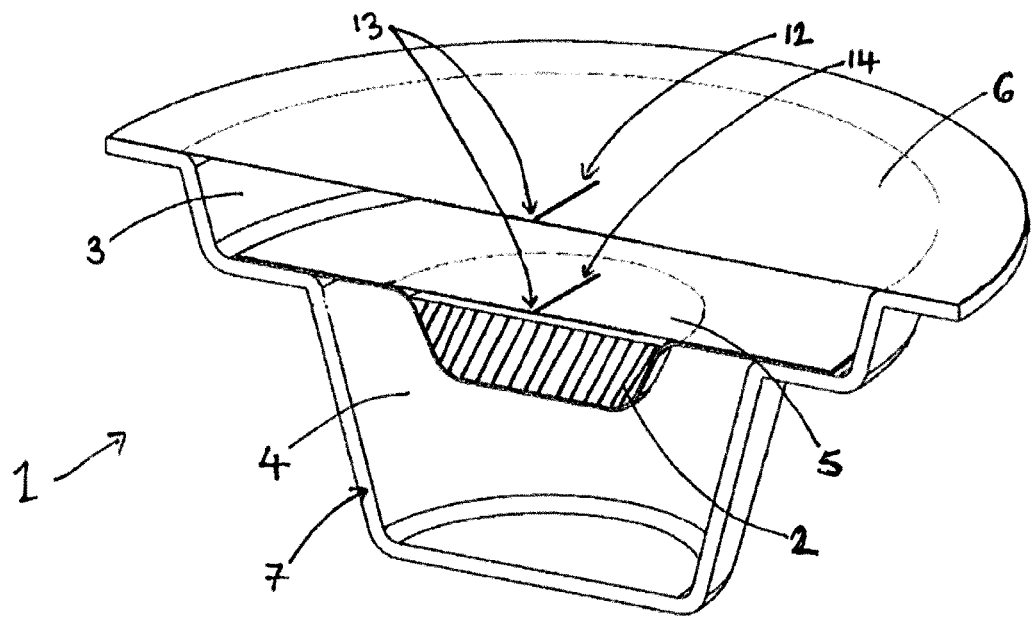
FIG. 4 shows a perspective view of a cross section through the apparatus of FIG. 1.
Figure 5:
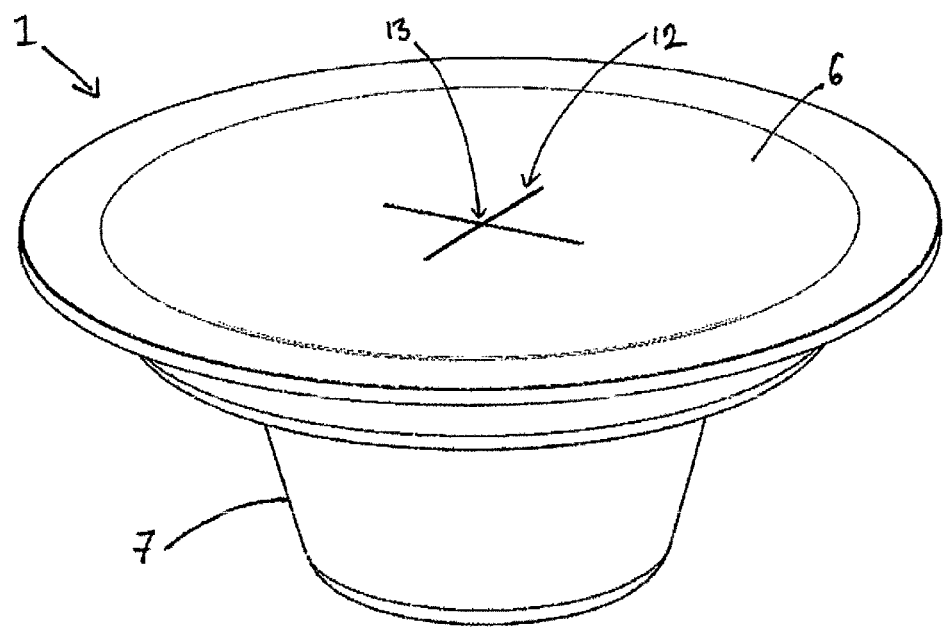
FIG. 5 shows a perspective view of the apparatus of FIG. 1.

FIG. 4 shows a perspective view of a cross section through the apparatus of FIG. 1 and FIG. 5 shows a perspective view of the apparatus of FIG. 1. It can be seen that apparatus has a generally circular shape.

Figure 6:
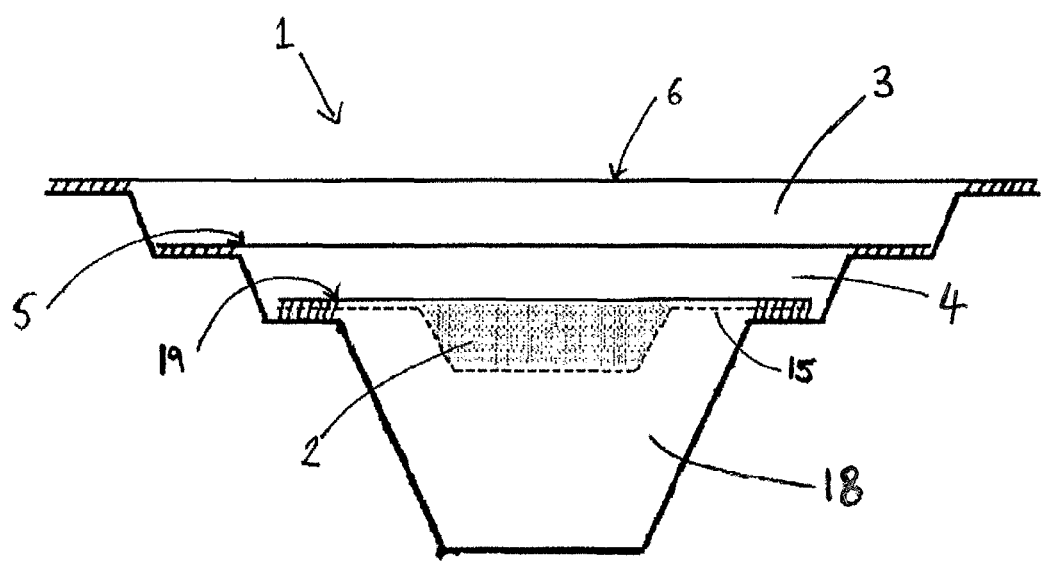
FIG. 6 shows a cross section through a second embodiment of an apparatus in accordance with the present invention.

FIG. 6 shows a cross-section of a second embodiment of an apparatus in accordance with the present invention. This second embodiment comprises the apparatus of the first embodiment with an additional third chamber 18 at a third pressure higher than atmospheric pressure.

In the second embodiment, the third chamber 18 is formed by a second separating wall 19 below the first separating wall 5. The second separating wall 19 is shared between the third chamber 18 and the second chamber 4. The powder 2 is held within the third chamber adjacent to the second separating wall 19. As in the first embodiment, the powder is held in a mesh container in the centre of the apparatus, away from the second external wall. The second separating wall 19 may have a point of weakness at an intended rupture position. The second separating wall may be kiss-cut, scored or laser etched at the intended rupture position.

In this embodiment the third pressure is higher than the first and second pressures in the first and second chambers. In particular, the third pressure is 600 kPa above atmospheric pressure, the second pressure is 400 kPa above atmospheric pressure and the first pressure is 200 kPa above atmospheric pressure. The first external wall 6 and first and second separating walls each have a threshold pressure of about 300 kPa (this may vary +/−50 kPa so the walls may burst anywhere between 250 kPa and 350 kPa).

This second embodiment is configured such that rupture of the first external wall 6 causes a drop in the pressure of the first chamber to atmospheric pressure, so that the pressure difference across the first separating wall becomes about 400 kPa exceeding its threshold pressure difference. This causes the catastrophic rupture of the first separating wall, in turn leading to the pressure difference across the second separating wall 19 exceeding the threshold pressure difference. This results in the catastrophic rupture of the second separating wall resulting in the expulsion and aerosolization of the powder.

In an alternative arrangement, the threshold burst pressure of each of the separating walls and first external wall may be about 300 kPa. The third pressure is 500 kPa above atmospheric pressure, the second pressure is 280 kPa above atmospheric pressure and the first pressure is 100 kPa above atmospheric pressure. In this arrangement both the first external wall and the first separating wall would have to be ruptured by the external element as rupturing only the first external wall would not lead to a sufficient pressure drop to burst the first separating wall. On rupturing the first separating wall the second separating wall would burst. This arrangement has the advantage that the pressure difference across each foil is lower making the apparatus more robust and less likely to leak or accidently burst.

So the three chamber configuration of this second embodiment has the potential advantage that, for a given strength of separating wall, one of the chambers can be pressurised to a higher pressure. As the pressure of chamber holding the powder is important to the powder aerosolization and the force with which the powder is ejected from the apparatus, it may be desirable to store the powder at a high pressure. Alternatively, the two-connecting-wall configuration may be more stable than the first embodiment for long term storage, as the desired second pressure can be maintained with lower pressure differentials across the separating walls than would be needed in a two-chamber device. This may be beneficial as lowering the pressure differentials may make apparatus less susceptible to leaks, and may make apparatus more robust and less likely to accidentally burst.

Figure 7:
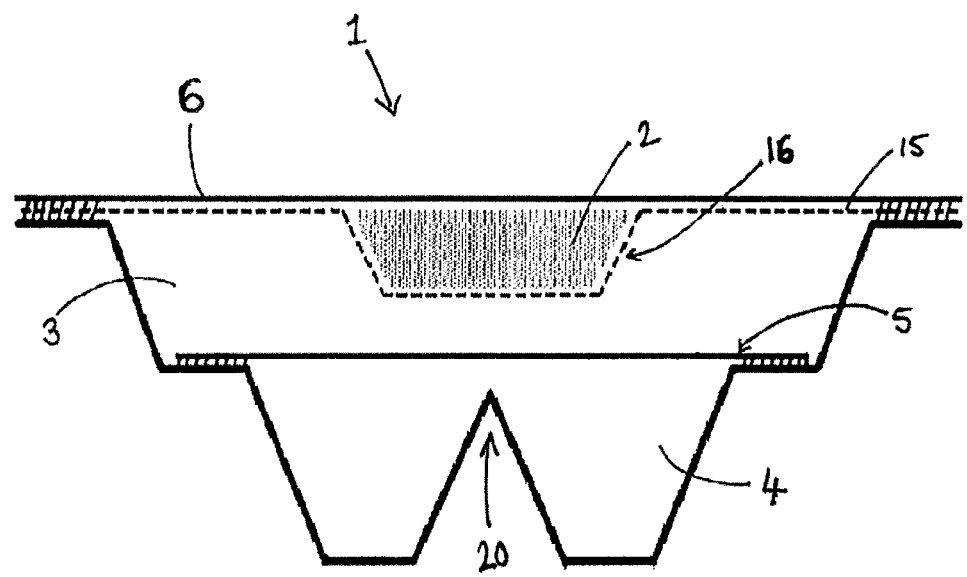
FIG. 7 shows a cross section through a third embodiment of an apparatus in accordance with the present invention.

FIG. 7 shows a third embodiment of the apparatus in accordance with the present invention. The apparatus of the third embodiment is the same as the apparatus of the first embodiment, but additionally comprises an internal piercing element 20 contained within the second chamber.

In the third embodiment of the apparatus, the powder is held on a gas-permeable material in the first chamber. The gas-permeable material is coupled to the first external wall.

Figure 8:
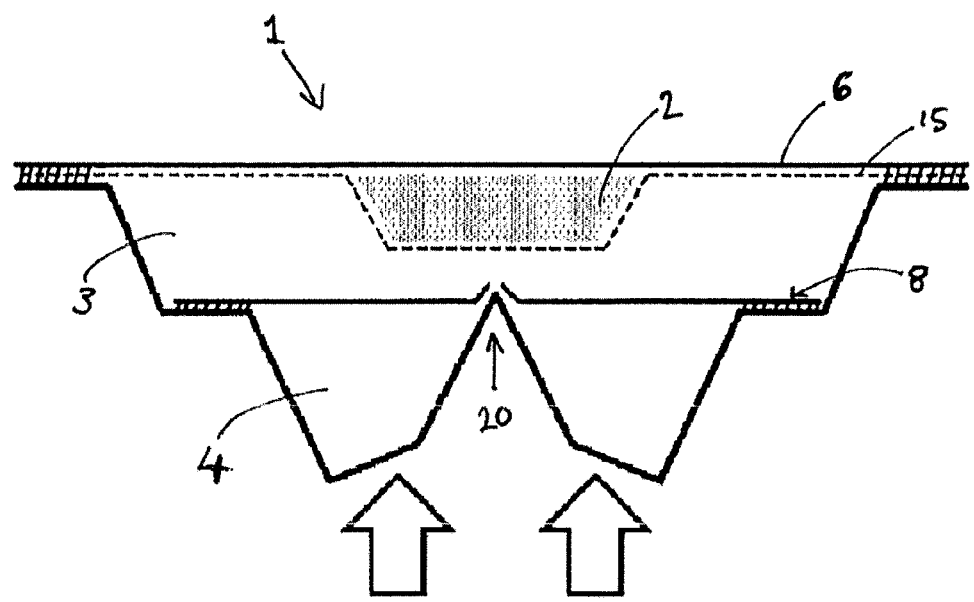
FIG. 8 shows a cross section through the apparatus of FIG. 7 as the separating wall of said apparatus is pierced by an internal piercing element.
Figure 9:
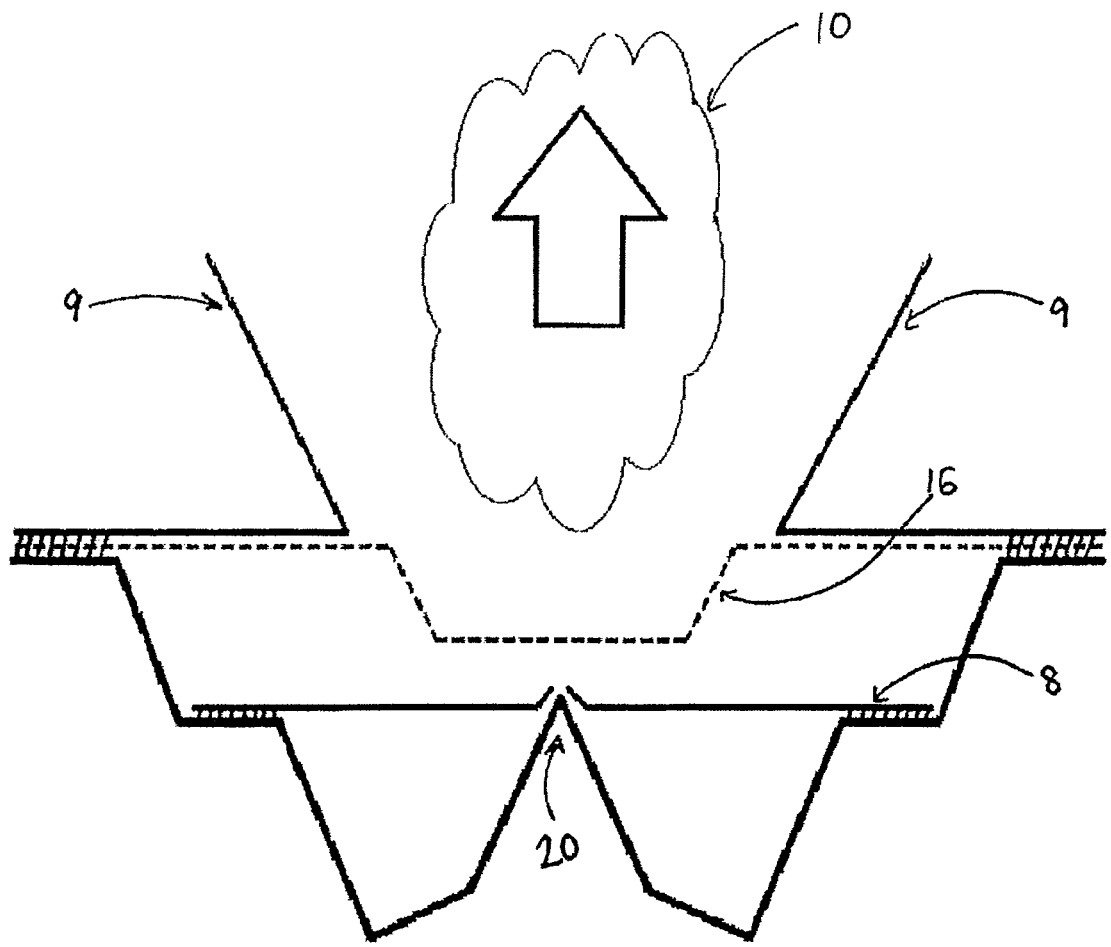
FIG. 9 shows a cross section through the apparatus of FIG. 7 immediately following piercing by an internal piercing element as shown in FIG. 8.

FIG. 7 shows that the internal piercing element 20 is formed in the base of the second chamber as part of the cold-forming or thermo-forming process, so that its sharper end points towards the separating wall 5. An application of pressure to the base of the apparatus causes the internal piercing element 20 to contact and break the separating wall, as shown in FIG. 8. Gas at the higher second pressure then expands rapidly into the first chamber, equalising the pressures in the two chambers. The apparatus is configured so that the newly equalised pressure exceeds the threshold pressure of the first external wall, which therefore ruptures catastrophically. FIG. 9 shows this catastrophic rupture, as an aerosolized cloud of powder is ejected from the apparatus.

This third embodiment is configured such that the difference between the first pressure and atmospheric pressure is less than the threshold pressure difference of the first external wall, but the difference between the second pressure and atmospheric pressure is significantly greater than the threshold pressure difference of the second external wall. The pressures and volumes of the first and second chambers are chosen so that, after rupture of the separating wall, the equalised pressure exceeds the threshold pressure difference of the first external wall.

Figure 10:
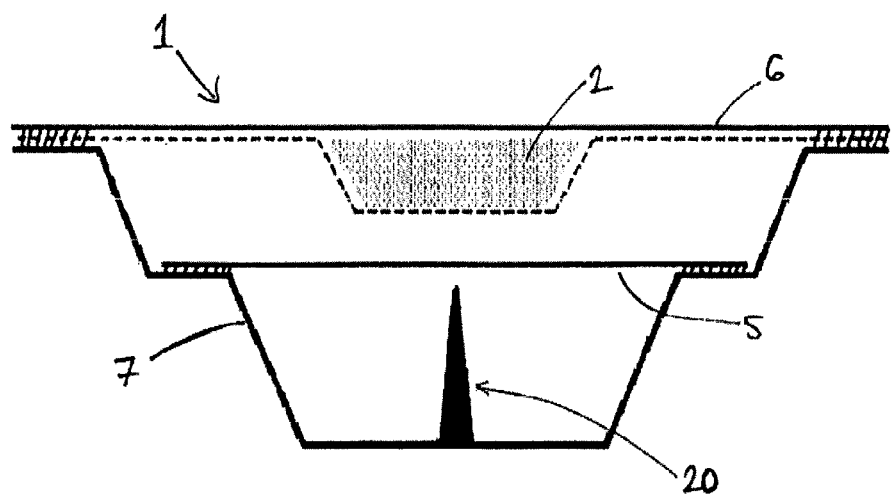
FIG. 10 shows a cross section through a further alternative embodiment of an apparatus in accordance with the present invention.

FIG. 10 shows a further embodiment comprising the internal piercing element 20, in which the internal piercing element comprises a separately formed spike bonded onto the internal side of the second external wall of the apparatus. The spike may be formed from a plastic such as ABS or from a metal.

Figure 11:
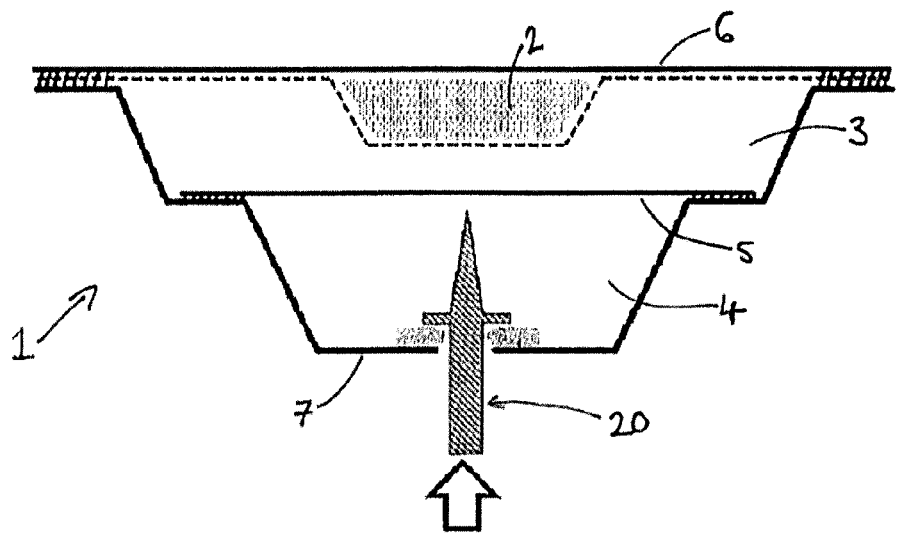
FIG. 11 shows a cross section through another alternative embodiment of an apparatus in accordance with the present invention.

FIG. 11 shows another embodiment in which the piercing element comprises a separate sliding piercer, which can slide into the second chamber through a gap in the second external wall. An airtight seal is formed around the shaft of the piercer so that the second chamber remains pressurised. This embodiment has the advantage that a lower force is required to make the piercing element contact the separating wall.

The operation of the apparatus shown in FIGS. 10 and 11 is very similar to the apparatus illustrated in FIGS. 7-9. The application of pressure to a rear of the apparatus results in rupture of the separating wall and thereafter expulsion of the powder as the first external wall bursts catastrophically. It should be clear that the idea of an internal piercing element may equally be applied to an apparatus having three or more chambers as described in the second embodiment.

In all the described embodiments the pressures within each of the chambers and the threshold pressures of the walls can be varied, and can be the same as or different to one another. For example, all the chambers within the apparatus may be at the same pressure but the separating and external walls can be chosen to have different threshold pressures at which they burst. The volumes and relative volumes of each of the chambers can also be chosen to suit a particular application. The energy for aerosolization is approximately equal to the product of the pressure and volume.

A device and method to provide aerosolized powder delivery in accordance with the invention will now be described with reference to FIGS. 12 to 15. The device is a dry powder inhaler.

Figure 12:
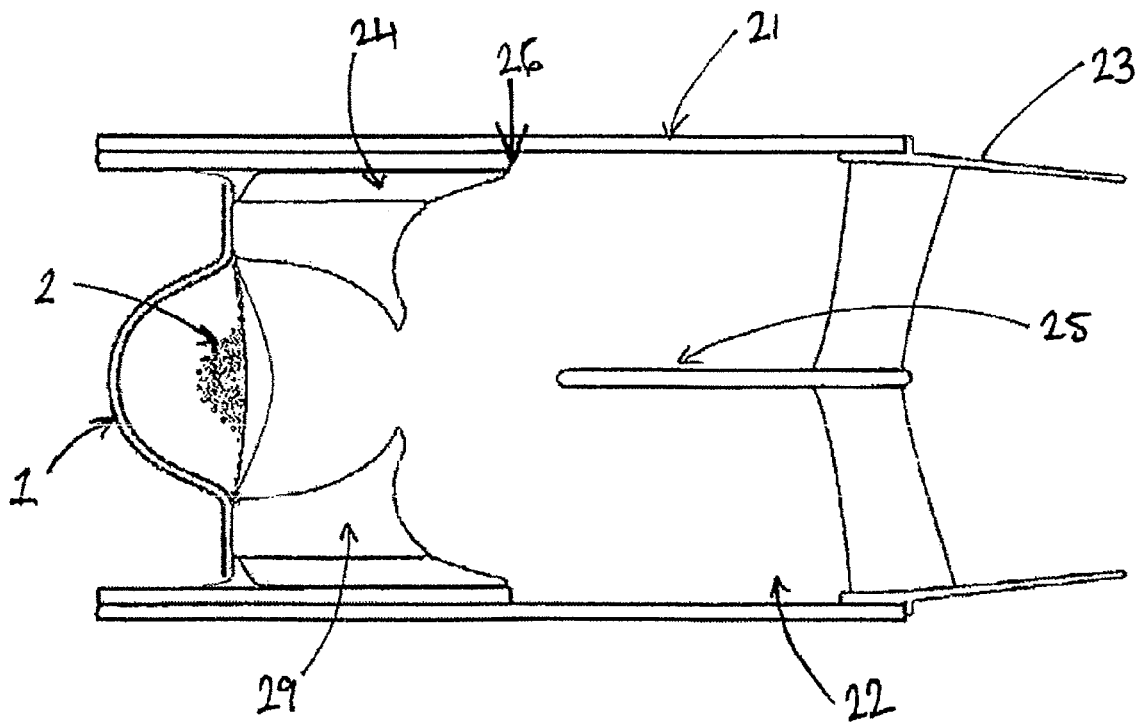
FIG. 12 shows a cross section through a drug delivery device embodying an aspect of the present invention.
Figure 13:
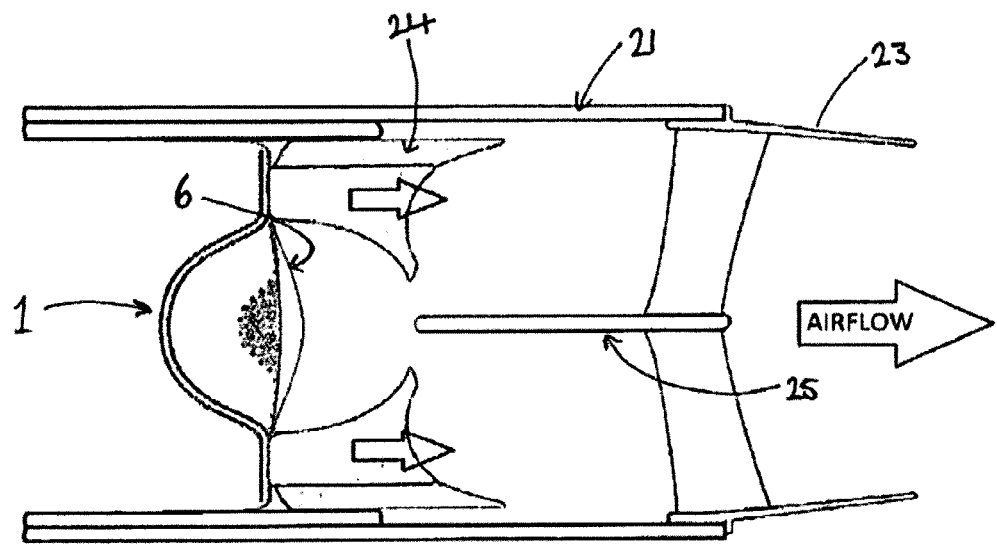
FIG. 13 shows a cross section through the device of FIG. 12 during actuation by inhalation.

FIG. 12 shows a cross-section of a first embodiment of the device in accordance with the present invention. The device is suitable for use with the first or second embodiments of the apparatus of the first aspect of the present invention. In this embodiment, the device comprises a sliding carriage element 24 held within the housing. The device further comprises a pressing element 25 within the housing and positioned between the apparatus 1 and the mouthpiece 23. This pressing element is configured to break the first external wall 6 of the apparatus, when the apparatus and the pressing element contact with a predetermined force. The apparatus is held on the sliding carriage element, which can move within the housing from an initial position 26, in which the apparatus is held apart from the pressing element, to a delivery position 27 in which the apparatus contacts the pressing element. The housing may also include a carriage stop surface 28 to prevent the carriage moving beyond a stop position towards the mouthpiece and wherein the pressing element does not pierce the separating wall of the apparatus as the sliding carriage moves to the stop position. This allows the pressing element to puncture the first external wall of the apparatus only, so that the second chamber fails catastrophically.

The device shown also comprises a vortex generator element, or nozzle, 29 within the housing, such that an aerosolized powder exiting the apparatus is funnelled by the vortex generator element in order to form a vortex of aerosolized powder 30. This vortex generator element is provided on the sliding carriage element of the device. The vortex generator element is situated between the apparatus and the mouthpiece. The vortex generator element comprises a portion 31 configured to cause turbulence in the aerosolized drug. With this vortex generator in place, rupture of the apparatus with the pressing element causes the device to output an aerosolized powder as a vortex ring.

The device is configured such that suction on the mouthpiece moves the sliding carriage from the initial position to the delivery position. In this way, inspiratory energy is used only to release the energy stored in the apparatus, while the energy for aerosolization and drug delivery is actively provided by the apparatus.

Figure 14:
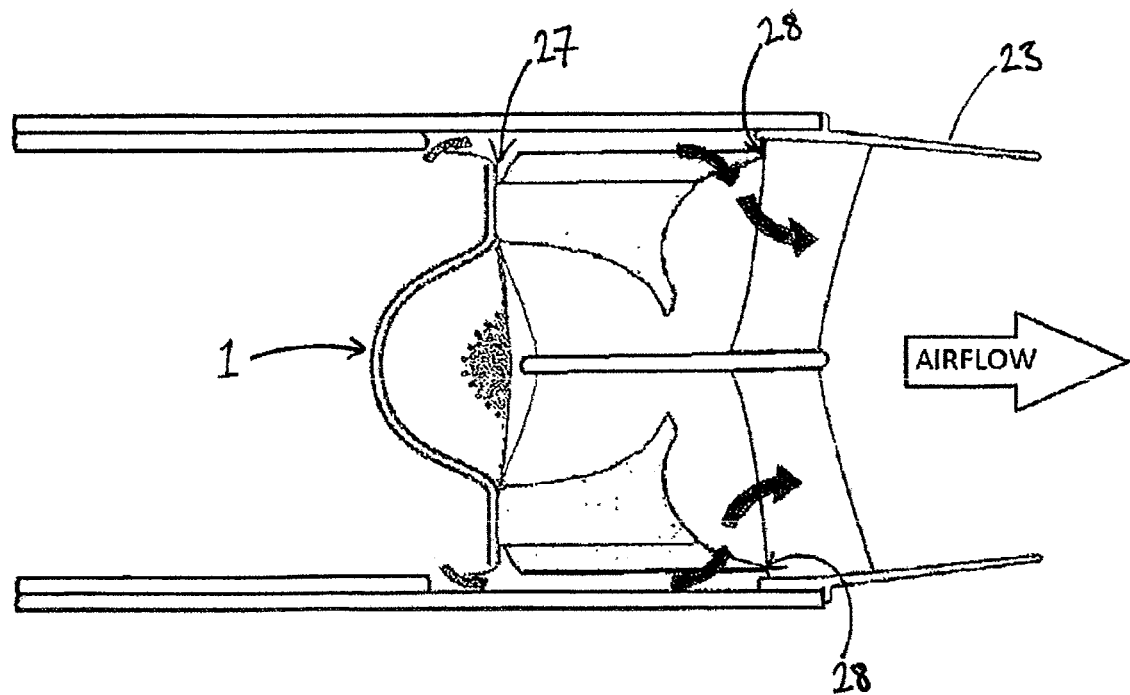
FIG. 14 shows a cross section through the device of FIG. 12 as the apparatus of FIG. 12 is pierced by a piercing element.

In the device shown in FIG. 12, the apparatus and the sliding carriage element occupy the whole cross section of the hollow body element, so as to form an airtight barrier. As shown in FIG. 14, inhalation via the mouthpiece therefore creates a low-pressure region between the mouthpiece 23 and the apparatus 1, causing the sliding carriage element to move towards the mouthpiece.

Figure 15:
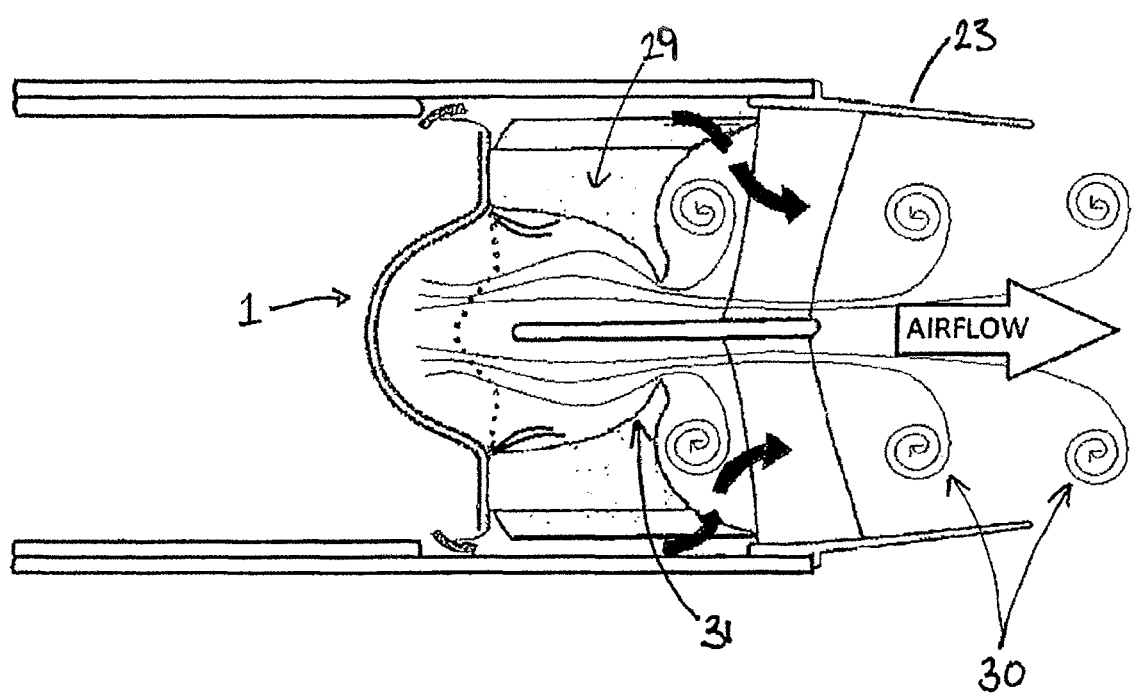
FIG. 15 shows a cross section through the device of FIG. 12 as aerosolized powder is delivered out of the device.

FIG. 15 shows that, when the sliding carriage element contacts the carriage stop surface 28 the apparatus is in the delivery position 27. As the apparatus reaches this position, the pressing element 25 contacts and ruptures only the first external wall of the apparatus, allowing the separating wall 5 to burst catastrophically as intended. Once the sliding carriage element has abutted the carriage stop surface, the sliding carriage no longer forms an airtight barrier in the hollow body element, and air is free to flow round the sides of the apparatus and out through the mouthpiece. This allows the patient to inhale continuously throughout the powder delivery process, ensuring that their airways stay open to receive the delivered dose of powder.

FIG. 16 shows the function of the vortex generator element 29, as the apparatus 1 delivers a cloud of aerosolized powder to the user. The curved portion of the vortex generator element cause turbulence in the aerosol delivered out of the apparatus in such a way that the aerosolized powder forms a vortex ring on exiting the device.

A device according to this embodiment may be single-use, or may allow replacement of spent apparatus with new, unused apparatus, thus allowing the device to be re-used.

An alternative device would be suitable for use with an apparatus having an internal piercing element. The alternative device comprises a compression element within the housing to press a rear of the apparatus instead of a pressing element pressing the front of the apparatus as a means to break the separating wall of the apparatus. The apparatus remains stationary within the housing in use. When actuated, the compression element contacts and compresses the base of the apparatus, pushing the internal piercing element of the apparatus up into the separating wall.

The compression element may comprise a bi-stable valve, or a sprung mass configured to strike the base of the apparatus with a predetermined force. The compression element is ideally breath activated. Alternatively, the compression element may be a manually operated arrangement, such that a user's finger, or a plunger operated by the user, contacts the base of the apparatus and compresses the second external wall.

The invention claimed is:

1. An apparatus for use in aerosolized delivery of a powder, comprising:
    a first chamber, containing gas at a first pressure higher than atmospheric pressure;
    a second chamber, containing gas at a second pressure higher than atmospheric pressure;
    a powder contained within the first or second chamber;
    wherein the first chamber has a first external wall and a separating wall, the separating wall being shared with the second chamber, wherein the first external wall or the separating wall is configured to rupture if the pressure difference across it becomes equal to or greater than a threshold pressure difference;
    wherein the difference between the second pressure and atmospheric pressure is greater than the threshold pressure difference; and
    wherein the powder is held on a gas-permeable structure.

2. An apparatus according to claim 1, wherein the difference between the second pressure and the first pressure is less than the threshold pressure difference.

3. An apparatus according to claim 2, wherein the first external wall or separating wall has a point of relative weakness at an intended rupture position.

4. An apparatus according to claim 3, wherein the first external wall or separating wall is kiss-cut, scored or laser-etched at the intended rupture position.

5. An apparatus according to claim 2, wherein the first external wall comprises a laminated foil.

6. An apparatus according to claim 1, wherein the powder is formed into a pellet.

7. An apparatus according to claim 1, wherein the apparatus has a second external wall to which the separating wall is joined around its periphery, and wherein the powder is held apart from the second external wall, so that when the separating wall ruptures expanding gas from the second chamber flows both through and around the powder.

8. An apparatus according to claim 1, wherein the powder is held in the second chamber.

9. An apparatus according to claim 1, wherein the gas-permeable structure is a mesh material.

10. An apparatus according to claim 1, wherein the gas-permeable structure is held close to the separating wall or the first external wall.

11. An apparatus according to claim 1, wherein the first pressure is equal to the second pressure.

12. An apparatus according to claim 1, wherein the pressure difference between the second pressure and atmospheric pressure is at least 20% greater than the threshold pressure.

13. An apparatus according to claim 1, wherein the first pressure is lower than the second pressure.

14. An apparatus according to claim 1, wherein the pressure in the second chamber is at least 50 kPa above atmospheric pressure.

15. An apparatus according to claim 1, wherein the threshold pressure difference is between 50 kPa and 1000 kPa.

16. An apparatus according to claim 1, wherein the chamber containing the powder is filled with a gas or gases that do not react with the powder during storage.

17. An apparatus according to claim 1, wherein the separating wall is formed from a laminated foil.

18. An apparatus according to claim 1, comprising a third chamber containing a fluid at greater than atmospheric pressure.

19. An apparatus according to claim 1, comprising an internal piercing element configured to rupture the separating wall, causing fluid communication between the first and second chambers.

20. An apparatus according to claim 7, wherein the first external wall or the second external wall of the apparatus is formed as a deep drawn can.

21. An apparatus according to claim 1, wherein the powder comprises a therapeutic agent.

22. An apparatus according to claim 21, wherein the powdered medicament is an active pharmaceutical ingredient.

23. A method for providing aerosolized powder delivery, comprising the steps of:
    acting on the apparatus of claim 1 to break one of the first external wall or separating wall, so that a pressure difference across the other of the first external wall or the separating wall exceeds the threshold pressure difference;
    wherein the step of acting on the apparatus comprises moving the apparatus relative to a pressing or piercing element to bring the apparatus into contact with the pressing or piercing apparatus.

24. A method according to claim 23, wherein the step of moving comprises moving the pressing or piercing element.

25. A method according to claim 23, wherein the step of acting on the apparatus comprises compressing the apparatus.

26. A device to provide aerosolized powder delivery, comprising:
    an apparatus in accordance with claim 1;
    a housing, including a hollow body element, with a mouthpiece disposed at a first end of the hollow body element;
    means to break one of the first external wall or the separating wall of the apparatus, so that a pressure difference across the other of the first external wall or the separating wall exceeds the threshold pressure difference.

27. A device according to claim 26, wherein the means to break is actuated by a user sucking on the mouthpiece.

28. A device according to claim 26, wherein the means to break is a pressing element.

29. A device according to claim 28, wherein the device additionally comprises:
    a sliding carriage element held within the housing, the apparatus being held on the sliding carriage element;
    wherein the pressing element is positioned within the housing,
    wherein the sliding carriage can move within the housing from an initial position in which the apparatus is held apart from the pressing element to a delivery position in which the apparatus contacts the pressing element.

30. A device according to claim 29, wherein the device is configured such that suction on the mouthpiece moves the sliding carriage from the initial position to the delivery position.

31. A device according to claim 29, wherein the pressing element is positioned between the sliding carriage and the mouthpiece.

32. A device according to claim 29, wherein the housing includes a carriage stop surface to prevent the carriage moving beyond a stop position towards the mouthpiece, and wherein the pressing element does not pierce the chamber containing the powder as the sliding carriage moves to the stop position.

33. A device according to claim 29, wherein the sliding carriage is free to recoil when the apparatus ruptures.

34. A device according to claim 26, further comprising a vortex generator element within the housing, such that an aerosolized drug formulation exiting the apparatus is funneled by the vortex generator element in order to form a vortex of aerosolized drug.

35. A device according to claim 34, wherein the vortex generator is provided on the sliding carriage.

36. A device according to claim 26, wherein the means to break is a compression element configured to compress a surface of the apparatus furthest from the mouthpiece.

37. A device according to claim 36, wherein the means to break is a spring loaded compression element that is released by a user sucking on the mouthpiece.

* * * * *